United States Patent
Unetich et al.

(10) Patent No.: US 8,489,201 B2
(45) Date of Patent: Jul. 16, 2013

(54) SHIELDED DIATHERMY APPLICATOR WITH AUTOMATIC TUNING AND LOW INCIDENTAL RADIATION

(75) Inventors: Robert M. Unetich, Pittsburgh, PA (US); James Hanlon, South Park, PA (US)

(73) Assignee: ReGear Life Sciences, Inc., Pittsburgh, PA (US)

( * ) Notice: Subject to any disclaimer, the term of this patent is extended or adjusted under 35 U.S.C. 154(b) by 275 days.

(21) Appl. No.: 12/796,778

(22) Filed: Jun. 9, 2010

(65) Prior Publication Data

US 2011/0060391 A1    Mar. 10, 2011

Related U.S. Application Data

(60) Provisional application No. 61/185,393, filed on Jun. 9, 2009.

(51) Int. Cl.
*A61F 2/00* (2006.01)
*A61N 1/00* (2006.01)
*A61B 18/04* (2006.01)

(52) U.S. Cl.
USPC ........... 607/101; 607/103; 607/152; 607/155; 606/33

(58) Field of Classification Search
USPC ............ 607/100–103, 108, 152–156; 606/27, 606/33, 34, 41, 45–50; 250/505.1–519.1; 336/84 R, 84 C; 331/67; 361/437, 220, 816, 361/818; 174/350–394
See application file for complete search history.

(56) References Cited

U.S. PATENT DOCUMENTS

| | | | |
|---|---|---|---|
| 4,068,292 A | 1/1978 | Berry et al. | |
| 5,107,832 A | 4/1992 | Guibert et al. | |
| 5,160,828 A | 11/1992 | Olsen | |
| 6,094,599 A | 7/2000 | Bingham et al. | |
| 6,471,695 B1 * | 10/2002 | Behl | 606/32 |
| 6,735,481 B1 | 5/2004 | Bingham et al. | |
| 6,853,865 B2 | 2/2005 | Beens et al. | |
| 7,769,468 B2 * | 8/2010 | Turner et al. | 607/100 |
| 2002/0040233 A1 | 4/2002 | George et al. | |
| 2004/0119033 A1 | 6/2004 | George et al. | |
| 2004/0230226 A1 | 11/2004 | Bingham et al. | |
| 2006/0119462 A1 | 6/2006 | Beens et al. | |
| 2008/0215115 A1 | 9/2008 | Bingham et al. | |
| 2010/0305560 A1 * | 12/2010 | Peterson | 606/33 |

* cited by examiner

*Primary Examiner* — Linda Dvorak
*Assistant Examiner* — Adam Avigan
(74) *Attorney, Agent, or Firm* — The Webb Law Firm

(57) ABSTRACT

An applicator supplying RF power for therapeutic diathermic treatment of a patient includes a radiation shielding device for shielding the applicator against misapplication of radiation to objects in the surroundings and unintended areas of the patient's body, and a coupling device for electrically coupling the radiation shielding device to at least one point of the body of a patient in a low impedance manner that reduces the potential drop from the grounded radiation shield to the body tissue.

8 Claims, 6 Drawing Sheets

SHIELDED DIATHERMY APPLICATOR WITH AUTOMATIC TUNING AND LOW INCIDENTAL RADIATION

CROSS-REFERENCE TO RELATED APPLICATION

This application claims priority from U.S. provisional application 61/185,393, entitled "SHIELDED DIATHERMY APPLICATOR WITH AUTOMATIC TUNING AND LOW INCIDENTAL RADIATION," filed Jun. 9, 2009, which is incorporated herein by reference.

BACKGROUND OF THE INVENTION

1. Field of the Invention

This invention relates to the field of bioelectromagnetics, specifically, the conversion of radio frequency (RF) energy in human or animal tissue to achieve therapeutic purposes both thermal and athermal. It represents advancements in equipment design that substantially reduce the incidental radiation of energy, while improving the consistency of energy conversion within the desired target tissue.

2. Description of Related Art

RF coil diathermy systems utilize coils to radiate both electric and magnetic fields. The proximity of the coils to the target tissue results in concentration of the electric and magnetic fields generated by RF excitation of the coils and energy conversion in the tissues near the coils. A problem with these coils is that significant fields can also exist at distances away from the coils, which can cause RF energy conversion within other tissue, exposure to workers nearby, and exposure to others in the general vicinity of the coils. It would, therefore, be desirable to provide an RF coil diathermy system that avoids the foregoing problems.

SUMMARY OF THE INVENTION

Disclosed is an applicator apparatus for supplying RF power for therapeutic diathermic treatment of a patient. The applicator includes radiation shielding for shielding the applicator against misapplication of radiation to objects in the surroundings and unintended areas of the patient's body, and a coupling device for electrically coupling the radiation shielding device to at least one point of the body of the patient in a low impedance manner.

The radiation shielding can include a conductive grid and at least one conductive pad electrically connected to the conductive grid to provide capacitive coupling to the body of the patient at least at one point. The periphery of the radiation shielding can curve or wrap around the non-applying areas of the applicator to form a curved conductive grid having radial spurs or fingers. The conductive pads can be circular in shape and can be connected at the electrical termination of each radial spur or finger of the curved conductive grid.

The conductive grid can include a substrate comprised of printed circuit material. The conductive grid can include an electrically conductive pattern disposed on a flexible, insulative substrate.

Also disclosed is a method of constructing a radiation shielded diathermy applicator device. The method includes providing a radio frequency diathermy applicator device including a first flexible coil structure, a second flexible coil structure, and a first non-conductive spacer between the first and second flexible coil structures. The method also includes providing a second non-conductive spacer disposed between the first flexible coil structure and a radiation shield that includes an electrically conductive grid pattern on a flexible, insulative substrate having radial fingers, wherein the electrically conductive grid pattern includes conductive pads on the radial fingers; and wherein said radial fingers can be curved around the first non-conductive spacer, the first flexible coil structure, and the second non-conductive spacer, and coupled to the first non-conductive spacer, wherein said conductive pads are positioned on the first non-conductive spacer on a surface thereof opposite the first flexible coil structure.

It should be understood that the following descriptions, while indicating various embodiments of the invention and numerous specific details thereof, are given by way of illustration and not of limitation. Many substitutions, modifications, additions and/or rearrangements may be made within the scope of the invention without departing from the spirit thereof, and the invention includes all such substitutions, modifications, additions and/or rearrangements.

DETAILED DESCRIPTION OF THE INVENTION

The invention and the various features and advantageous details thereof are explained more fully and illustrated by the accompanying drawings and detailed in the following description.

Figure 1A:
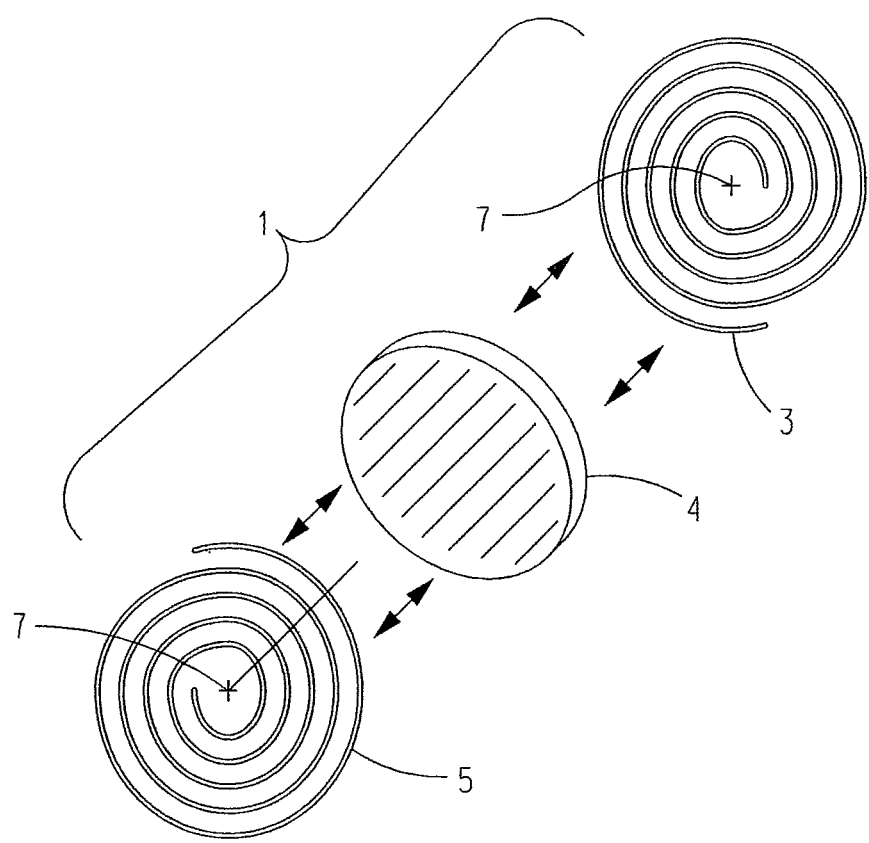
FIG. 1A is an exploded perspective view of a flexible coil structure of a prior art radio frequency diathermy device.

Referring to FIG. 1A, a prior art flexible coil structure 1, like the one shown in U.S. 2006/0119462, which is incorporated herein by reference, includes a secondary flexible coil structure 5 having a flexible, spiral-like winding which is physically coupled or positioned in spaced relation to a primary flexible coil structure 3 that also has a flexible, spiral-like winding, and a non-conductive spacer 4 disposed between and in contact with both primary flexible coil structure 3 and secondary flexible coil structure 5.

Figure 1B:
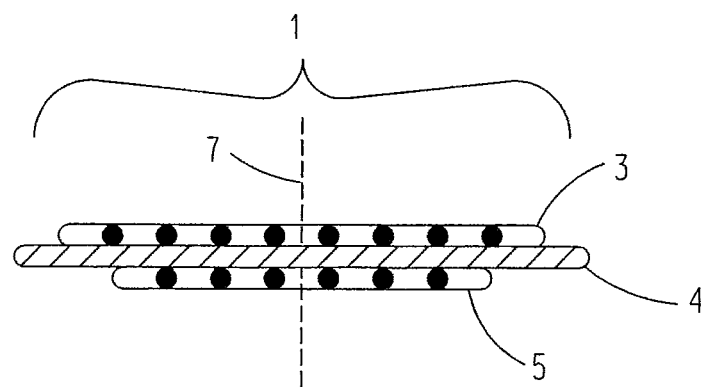
FIG. 1B is a cross-sectional view of the radio frequency diathermy device of FIG. 1A in an assembled state.

Referring to FIG. 1B, in an unflexed state, coil structures 3, 5 are two-dimensional spirals, each occupying a separate plane. Desirably, these separate planes are parallel to each other with spacer 4 disposed between and coupled to both coil structures 3, 5. Desirably, coil structures 3, 5 have a common central axis 7 and are positioned in spaced relation along central axis 7. In one, non-limiting embodiment, coil structures 3, 5 include 18-gauge stranded silver-plated copper wire disposed on a sheet or substrate of insulative polytetrafluoroethylene (PTFE). Other types of wires and insulative sheets would also be acceptable.

Figure 2:
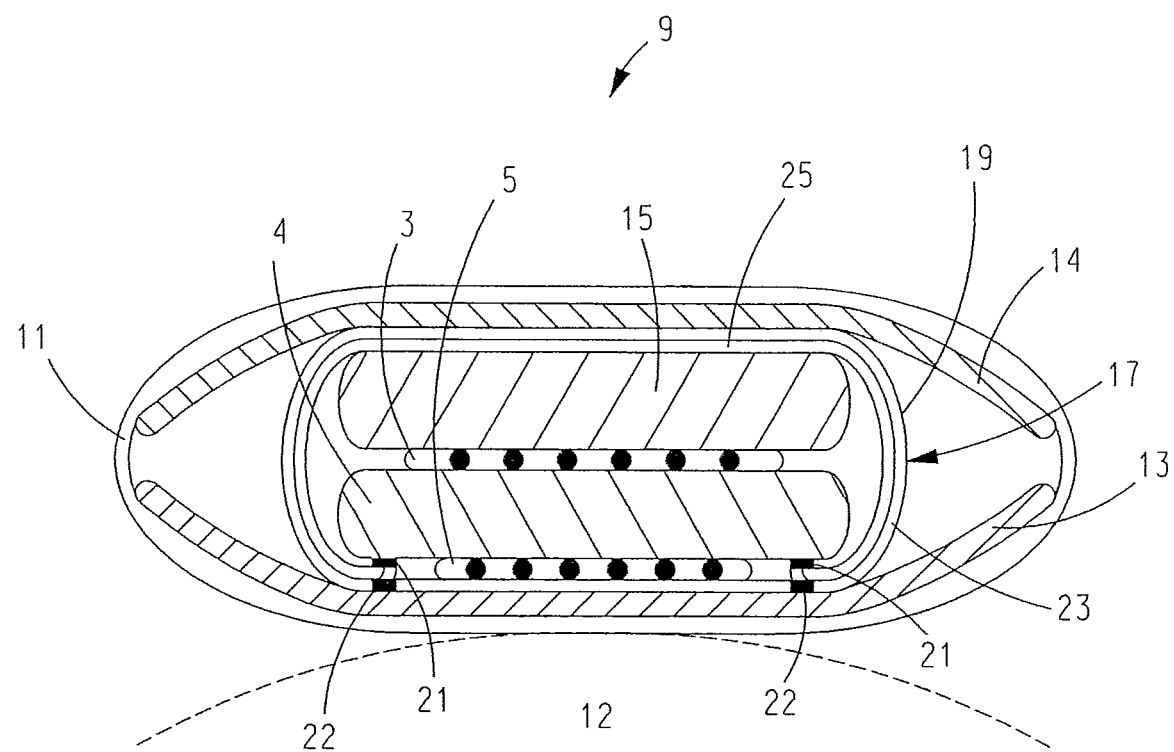
FIG. 2 is a cross-sectional view of a radiation shielded diathermy applicator in accordance with the present invention coupled to the body of a patient or treatment target.

Referring to FIG. 2, a cross-sectional view of a radiation shielded diathermy applicator 9 coupled to a patient 12 or treatment target is depicted. The exterior of applicator 9 is a non-conductive, flexible pouch 11 which allows applicator 9 to conform to a patient's chest, abdomen, back, and/or neck. Desirably, pouch 11 is made from nylon. However, this is not to be construed as limiting the invention.

Applicator 9 is in the form of a pad-shaped structure that includes a non-conductive layer 13 that separates pouch 11 from secondary flexible coil structure 5 contained within the pad structure of applicator 9. Applicator 9 also includes a non-conductive layer 14 that separates a radiation shield 17 (described hereinafter) from pouch 11.

Secondary flexible coil structure 5 is embedded or disposed between layer 13 and spacer 4. Primary flexible coil structure 3 is embedded or disposed between spacer 4 and a non-conductive radiation shield spacer 15. Spacer 4 separates secondary flexible coil structure 5 from primary flexible coil structure 3. Layer 13 provides space between patient 12 and secondary flexible coil structure 5 when applicator 9 is being used by patient 12.

Desirably, layer 13, layer 14, spacer 4, and radiation shield spacer 15, are each made from closed-cell polyethylene foams with thermoresistance, although other types of flexible, insulative material would also be acceptable. In one embodiment, layer 13, layer 14 and spacer 4 are made of foam having a thickness of 9.525 mm, and radiation shield spacer 15 is a foam layer having a thickness of 31.75 mm. However, other thicknesses and materials would also be acceptable.

Figure 3:
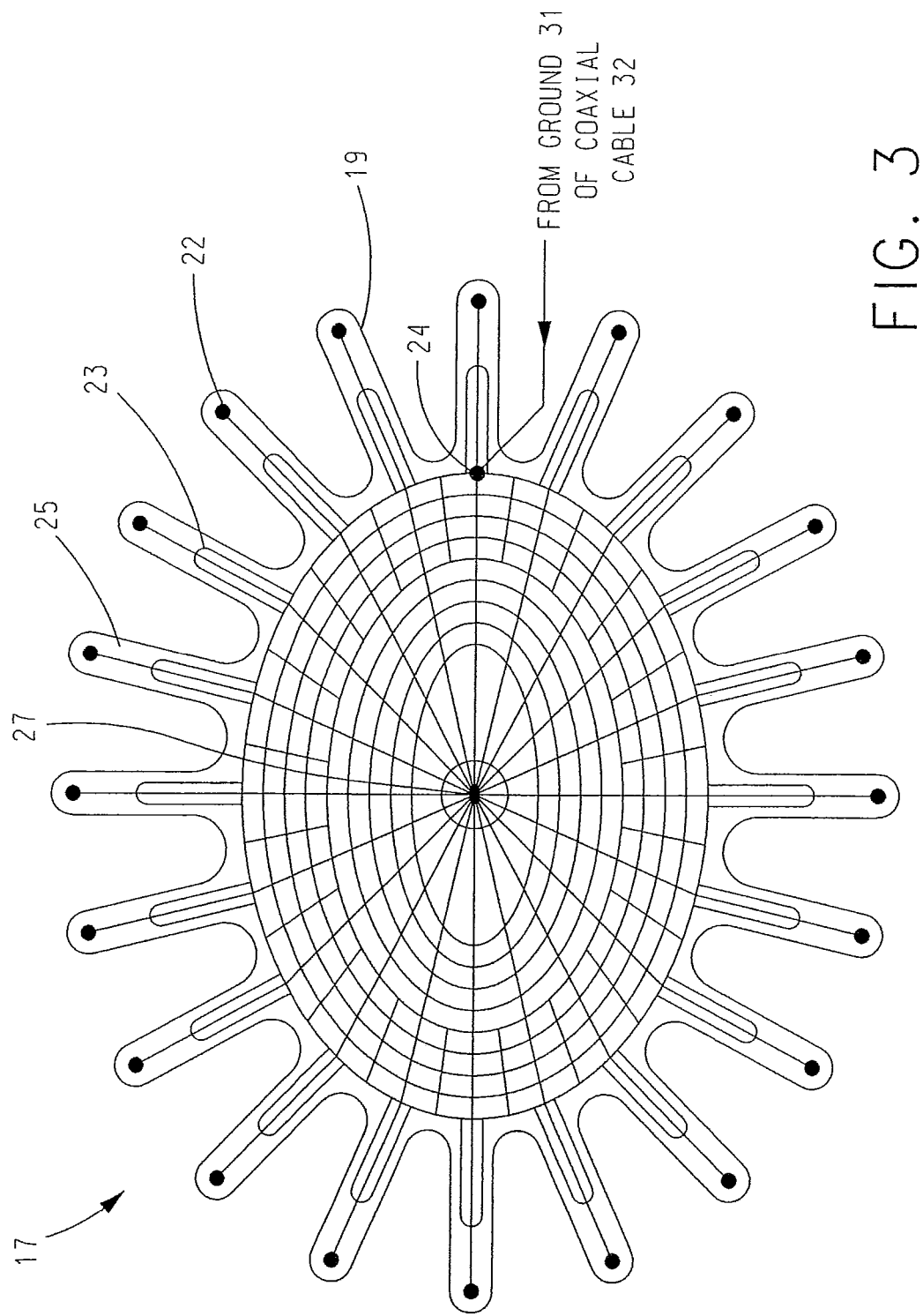
FIG. 3 is a radiation shielding device of the applicator of FIG. 2.

With reference to FIG. 3 and continuing reference to FIG. 2, radiation shield 17 covers the non-patient facing side of radiation shield spacer 15 and has radial fingers 19 that curve around radiation shield spacer 15, primary flexible coil structure 3, spacer 4, and connect to the patient-facing side of spacer 4. Desirably, Velcro® 21 is used to connect each radial finger 19 to spacer 4. However, this is not to be construed as limiting the invention since it is envisioned that any other suitable and/or desirable means can be utilized to connect each finger to spacer 4. At the end of each radial finger 19 is a conductive pad 22 that faces the body part of patient 12 under treatment when applicator 9 is worn by a patient. Desirably, each pad 22 provides capacitive coupling to the body of the patient 12. Radiation shield 17 also includes a conductive pad 24 which is coupled to a ground reference, e.g., a ground 31 sheath of coaxial cable 32 (shown in FIG. 4) in use of radiation shield 17.

Radiation shield 17 includes conducting tracks 23 formed on a flexible printed circuit material made of a flexible, insulative substrate 25. Conducting tracks 23 are also disposed on substrate 25 and electrically coupled to conductive pads 22 and conductive pad 24. Non-limiting examples of materials that can be used for this substrate include FR-4, G-10, or Kapton®. Kapton® is a registered trademark of E.I. du Pont de Nemours and Company. Desirably, radiation shield 17 has the grid-like pattern of conducting tracks 23 shown in FIG. 3. However, this is not to be construed as limiting the invention as it is envisioned that any suitable and/or desirable pattern having the same effect as the grid-like pattern shown in FIG. 3 can be used. It should also be noted that other materials could be substituted for substrate 25 provided that any such material has sufficient flexibility and dielectric strength.

Desirably, radiation shield 17 adds only a small amount of stray capacitance across secondary flexible coil 5 while allowing electric field lines to terminate on the radiation shield conducting tracks 23, which are coupled to a ground reference via conducting pad 24 coupled to the ground sheath 31 of coaxial cable 32. Desirably, radial fingers 19 of radiation shield 17 remain constant in width as the radius of the radial fingers 19 increases radially from the center axis 27 of the radiation shield 17. The pattern of radial fingers 19 on the periphery allows the fingers to be curved around shield spacer 15, primary flexible coil structure 3, and spacer 4. The conductive pads 22 at the ends of radial fingers 19 define capacitive coupling elements that are positioned in spaced relation to the body tissue of patient 12 when applicator 9 is worn by the patient 12. Each conductive pad 22 acts as one plate of a capacitor, with the body tissue of patient 12 acting as a second plate of a capacitor, and layer 13 acting as a dielectric between each pad 22 and the body tissue of patient 12.

Conductive pads 22, along with the body of patient 12 and layer 13, form a capacitor which capacitively couples conductive tracks 23 to the patient's body 12. More specifically, each conductive pad 22 spaced from the body of patient 12 by layer 13 acts as a separate capacitor in parallel with the combination of each of the other pads 22 spaced from the body of patient 12 by layer 13. When multiple conductive pads 22 come into close proximity (spaced relation) with the body of patient 12 to form multiple parallel capacitors, these parallel capacitors act as a single large capacitor. Radiation shield 17 therefore avoids RF radiation fields from emanating to the surrounding environments by capacitively coupling these fields to the body of patient 12.

Figure 4:
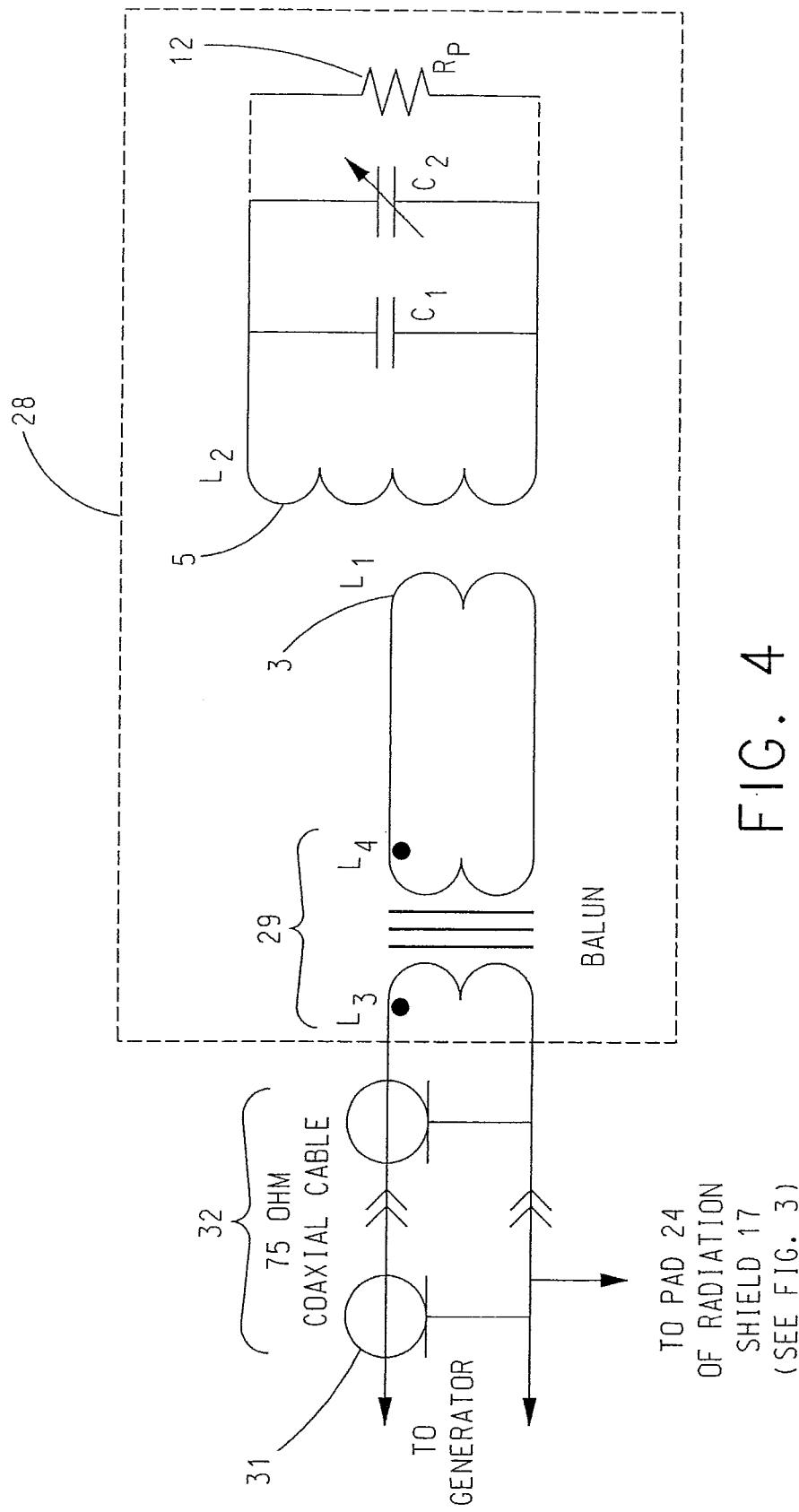
FIG. 4 is an electrical schematic diagram of an RF diathermy device.

Referring to FIG. 4, an electrical schematic diagram including supporting circuitry used with primary and secondary flexible coil structures 3, 5 in an RF diathermy device 28 is shown. Resistor $R_p$ is a representation of the body of patient 12. Inductor $L_2$ is a representation of secondary flexible coil structure 5 and inductor $L_1$ is a representation of primary flexible coil structure 3. Capacitor $C_1$ is a representation of the capacitance that exists by the spacing among patient 12, primary flexible coil structure 3, and secondary flexible coil structure 5. The capacitance of capacitor $C_1$ may also include the capacitance of conductive pads 22 adjacent the body of patient 12. Capacitor $C_2$ is a variable capacitor that can be connected in parallel with $R_p$ and $C_1$. Capacitor $C_2$ enables tuning by matching the impedance of the combination of $C_1$, $C_2$, $L_2$, and $R_p$ to the impedance of supporting circuitry so the same impedance can be realized throughout diathermy device 28 regardless of the patient 12 coupled to the device 28. This impedance matching allows the resonant frequency of the combination of $C_1$, $C_2$, $L_2$, and $R_p$ to be about the same for each patient 12 that uses the device. An isolation device 29 (e.g. a balun) transforms an unbalanced input signal on the L3 side of device 29 into a balanced output signal on the L4 side of device 29, which output signal is supplied to primary flexible coil structure 3. Isolation device 29 acts to electrical isolate primary and secondary flexible coil structure 3 and 5 from a ground reference, such as, without limitation, the ground 31 of a 75 ohm coaxial cable 32, whereupon primary and secondary flexible coil structures 3 and 5 can "float" relative to said ground reference. Coaxial cable 32 connects the L3 side of device 29 to an RF generator.

Figure 5:
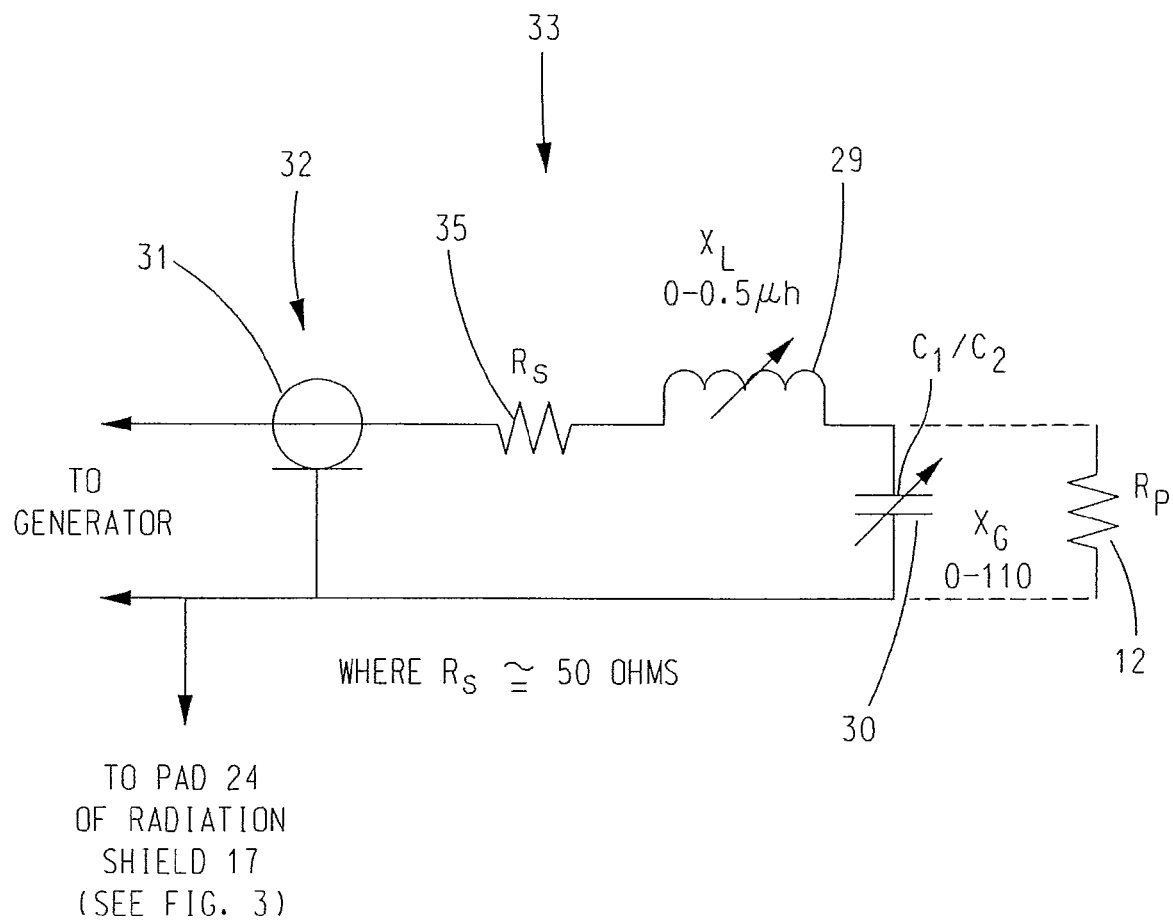
FIG. 5 is a lumped series tuned circuit model of the tuning circuit of FIG. 4.

Referring to FIG. 5, a lumped, series tuned model circuit 33 is depicted. The schematic depicted in FIG. 4 of RF diathermy applicator 28 can be reduced to create model circuit 33. In model circuit 33, resistor $R_p$ represents patient 12; variable capacitor 30 represents the lumped capacitance of applicator 28, including variable capacitor $C_2$; variable inductor 29 represents the lumped inductance of applicator 28, and resistor 35 represents the lumped resistance of applicator 28. These elements are connected to an RF generator (not shown) via coaxial cable 32. The tuning range of model circuit 33 may be selected so as to avoid resonance when body tissue is not coupled to applicator 9.

In model circuit 33, a resistive value $R_s$ of resistor 35 changes with tissue loading. Specifically, resistive value R, is lower when resistor 35 is unloaded and is higher when resistor 35 is "heavily loaded". Resistive value $R_s$ changes over a range of about 2:1 in practice and the resulting currents and voltages across the tuning circuit elements can then also be expected to vary as much as 2:1 at resonance and even more at detuned conditions. When model circuit 33 is properly matched and resonated, resistor 35 simplifies into a 50 ohm resistor. With 35 watts present, this represents a voltage of about 42 Volts rms and a current of 42/50~0.84 Amps. These RF currents and voltages are significant values to apply to a tuning circuit, and when model circuit 33 is unloaded, the values increase significantly since the current flowing increases due to the lower load resistance value.

Figure 6A:
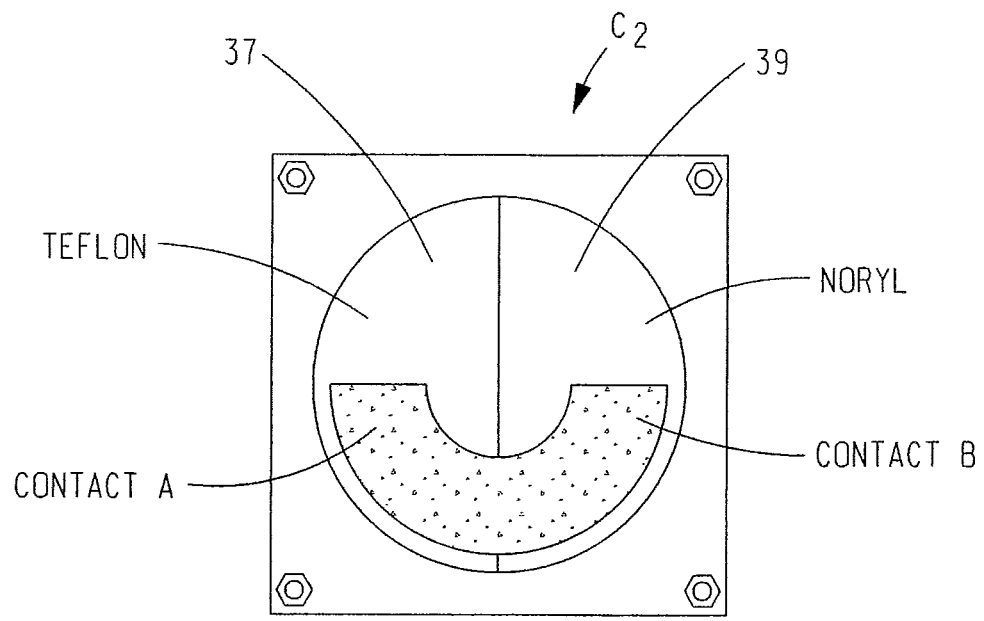
FIG. 6A is a plan view of the adjustable dielectric constant variable capacitor that can be used with the tuned circuit model of FIG. 5.
Figure 6B:
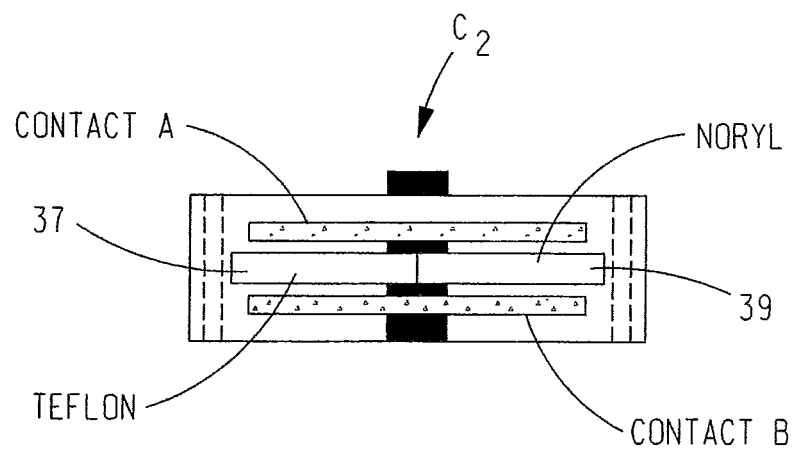
FIG. 6B is a cross-sectional view of the adjustable dielectric constant variable capacitor shown in FIG. 6A.

Referring to FIGS. 6A-6B, a non-limiting exemplary embodiment of variable capacitor $C_2$, shown in FIGS. 4 and 5, is depicted. Variable capacitor $C_2$ includes a moveable section of two low-loss dielectric materials 37, 39 that cause the average dielectric constant between the fixed metal plates (Contact A and Contact B) of capacitor $C_2$ to vary over a two-to-one range as the moveable section is rotated or moved between Contact A and Contact B. The materials 37, 39 selected in this particular embodiment are Teflon® and Noryl®, with approximate dielectric constants of 2 and 4, respectively. Teflon® is a registered trademark of E.I. du Pont de Nemours and Company. Noryl® is a registered trademark of Saudi Basic Industries Corporation (SABIC). It should be noted that other materials could be substituted for either of materials 37, 39, depending on the range of capacitance desired. Use of these materials avoids the need for the metal plates (i.e., Contact A and Contact B) to have a moveable electrical contact, greatly improving reliability and lowering cost. The construction of variable capacitor $C_2$ in one embodiment is a circular design. It should be noted that other mechanical arrangements (for example a linear array) could be utilized without affecting the intended scope of this invention.

Variable capacitor $C_2$ is used to tune the radio frequency of RF diathermy device 28 to resonance, the value of which depends upon stray capacitances across secondary flexible coil structure 5. The transformed impedance caused by variable capacitor $C_2$ varies from inductive to resistive and then to capacitive as the stray capacitances change and as variable capacitor $C_2$ is adjusted.

Numerous characteristics and advantages of the invention covered by this document have been set forth in the foregoing description. It will be understood, however, that this disclosure is, in many respects, only illustrative. Changes may be made in details, particularly in matters of scope, size, and arrangement of parts without exceeding the scope of the invention. The invention's scope is, of course, defined in the language in which the appended claims are expressed.

The invention claimed is:

1. An applicator apparatus supplying RF power for therapeutic diathermic treatment of a patient comprising:
   a radiation shielding device for shielding said applicator apparatus against misapplication of radiation to objects in the surroundings and unintended areas of the patient's body; and
   a coupling device for electrically coupling said radiation shielding device to at least one point of the body of said patient in a low impedance manner that reduces the potential drop from the grounded radiation shield to the body tissue, wherein:
   said radiation shielding device comprises a conductive grid;
   said coupling device comprises at least one conductive pad electrically connected to said conductive grid and providing capacitive coupling to the body of said patient at said at least one point;
   said conductive grid adjacent its periphery comprises radially extending spurs or fingers curved around the non-radiation-applying areas of the applicator; and
   each pad is adjacent the distal end of one radial spur or finger.

2. The apparatus of claim 1, wherein each pad has a circular shape.

3. The apparatus of claim 1, wherein said conductive grid is comprised of a substrate comprised of printed circuit material.

4. The apparatus of claim 1, wherein said conductive grid is comprised of an electrically conductive pattern disposed on a flexible, insulative substrate.

5. The apparatus of claim 4, wherein said electrically conductive pattern is coupled to a ground reference.

6. The apparatus of claim 4, wherein said substrate is FR-4, G-10, or a polyimide film.

7. A method of constructing a radiation shielded diathermy applicator device, comprising:
   providing a radio frequency diathermy applicator device comprising a first flexible coil structure, a second flexible coil structure, and a first non-conductive spacer between the first and second flexible coil structures;
   providing a second non-conductive spacer disposed between the first flexible coil structure and a radiation shield that includes an electrically conductive grid pattern on a flexible, insulative substrate having radial fingers, wherein the electrically conductive grid pattern includes conductive pads on the radial fingers; and wherein said radial fingers are curved around the first non-conductive spacer, the first flexible coil structure, and the second non-conductive spacer, and coupled to the first non-conductive spacer, wherein said conductive pads are positioned on the first non-conductive spacer on a surface thereof opposite the first flexible coil structure.

8. The method according to claim 7, wherein said flexible substrate is FR-4, G-10, or a polyimide film.

* * * * *